(12) United States Patent
Gehrig et al.

(10) Patent No.: US 8,698,510 B2
(45) Date of Patent: Apr. 15, 2014

(54) CAPACITIVE MEASURING CIRCUIT FOR YARN INSPECTION

(75) Inventors: Reto Gehrig, Winterthur (CH); Phillipp Ott, Steg (CH); Rolf Joss, Horgen (CH)

(73) Assignee: Uster Technologies AG, Uster (CH)

( * ) Notice: Subject to any disclaimer, the term of this patent is extended or adjusted under 35 U.S.C. 154(b) by 324 days.

(21) Appl. No.: 13/121,595

(22) PCT Filed: Oct. 12, 2009

(86) PCT No.: PCT/CH2009/000327
§ 371 (c)(1),
(2), (4) Date: May 20, 2011

(87) PCT Pub. No.: WO2010/043063
PCT Pub. Date: Apr. 22, 2010

(65) Prior Publication Data
US 2011/0254567 A1    Oct. 20, 2011

(30) Foreign Application Priority Data
Oct. 16, 2008 (CH) ........................... 1644/08

(51) Int. Cl.
*G01R 27/26* (2006.01)
*G01R 17/00* (2006.01)
(52) U.S. Cl.
USPC .......................... 324/663; 324/658

(58) Field of Classification Search
None
See application file for complete search history.

(56) References Cited

U.S. PATENT DOCUMENTS

| 3,757,211 A * | 9/1973 | Goto ............................ 324/671 |
| 3,879,660 A * | 4/1975 | Piso ............................. 324/663 |
| 3,967,196 A * | 6/1976 | Bennett ......................... 324/548 |
| 4,208,625 A * | 6/1980 | Piso ............................. 324/671 |
| 4,974,296 A * | 12/1990 | Vidler ........................... 19/239 |
| 6,346,819 B1 | 2/2002 | Joss et al. |
| 2008/0111563 A1 | 5/2008 | Ott et al. |

FOREIGN PATENT DOCUMENTS

| DE | 19535177 A1 | 3/1997 |
| EP | 1124134 A2 | 8/2001 |
| WO | 2007115416 A1 | 10/2007 |

* cited by examiner

*Primary Examiner* — Vinh Nguyen
(74) *Attorney, Agent, or Firm* — Luedeka Neely Group, P.C.; Rick Barnes

(57) ABSTRACT

A measuring circuit used for the capacitive examination of a moving elongated textile test material such as card sliver, roving, yarn or woven fabric, having a measuring capacitor for accommodating the test material, and a component with a capacitance which can be changed by an electric control signal. The measuring circuit can thus be balanced in a simple, rapid, cost-effective and especially automatic way.

13 Claims, 4 Drawing Sheets

CAPACITIVE MEASURING CIRCUIT FOR YARN INSPECTION

FIELD

The present invention lies in the field of the electric measuring circuits. It relates to a capacitive measuring circuit according to the preamble of the first claim and a method for operating a capacitive measuring circuit according to the preamble of a further independent claim. The invention allows automatic balancing of the measuring circuit, a simulation of measurements with the measuring circuit, a testing of the measuring circuit or a testing of components connected in series with the measuring circuit.

A preferred field of application for the invention is the capacitive testing of elongated, preferably textile structures such as a card sliver, roving, yarn or woven fabric. The invention thus also relates to an apparatus for the capacitive examination of a moved elongated test material according to the preamble of a further claim. The goal of such an examination can be for example the detection of foreign substances, the recognition of changes of the mass per unit of length and/or the measurement of humidity in the test material. The invention can be used for example in the production process (online) in yarn cleaners in spinning and bobbing winding machines or in laboratory tests (offline) in yarn testing devices.

BACKGROUND

A large number of various apparatuses are known for examining or testing elongated textile test materials such as a card sliver, roving, yarn or woven fabric for example. Depending on their application, they can be categorized into the two classes of laboratory test (offline) and testing during the production process (online). The apparatuses make use of the various known sensor principles, of which the capacitive measuring principle being of special interest in this case. A measuring circuit with a measuring capacitor which is arranged as a plate capacitor is provided. An electric alternating voltage is applied to the measuring circuit, through which an alternating electrical field is produced in the measuring capacitor. The test material is moved through the plate capacitor and is subjected to the alternating field. Dielectric properties of the test material are determined. The parameters of the test material such as mass per unit of length and/or material composition are determined from the dielectric properties. Examples for suitable measuring circuits and evaluation circuits for their output signals can be found in the specifications EP-0'924'513 A1, WO-2006/105676 A1 and WO-2007/115416 A1.

In order to enable the performance of precise measurements which are not influenced by external influences such as air temperature or air humidity, a compensation method is frequently applied. For this purpose, the measuring circuit contains a reference capacitor in addition to the actual measuring capacitor. It can be formed by adding a third capacitor plate for example which is arranged parallel to the two measuring capacitor plates and is electrically connected in series with them.

The measuring circuit should supply an output signal zero when an alternating voltage is applied without test material. Due to the various imperfections in real electric components, it is not sufficient in practice to arrange the measuring circuit symmetrically in order to obtain a zero signal without the test material. Each measuring circuit needs to be balanced individually for symmetrization. Symmetric balancing occurs in production by the manufacturer and optionally during maintenance by a service technician. For this purpose, the capacitance of at least one capacitance trimmer connected in parallel to the measuring circuit is usually changed. Trimming occurs manually with a suitable tool, e.g. a screwdriver. The known method of laser trimming is applied alternatively. In any case, the apparatus needs to be opened for the balancing. Such a manual balancing is laborious, time-consuming and expensive.

SUMMARY

It is therefore the object of the present invention to provide a measuring circuit which does not have the above disadvantages. The measuring circuit shall be capable of being balanced in a simple, rapid, cost-effective and especially automatic way. Furthermore, a method shall be provided for operating a measuring circuit in accordance with the invention. A capacitive apparatus for examining a moved elongated test material shall also be provided which is capable of being balanced in a simple, rapid, cost-effective and automatic way. It is a further object of the present invention to provide a method for simulating measurements with the measuring circuit, for testing the measuring circuit or for testing components connected in series with the measuring circuit.

These and other objects are achieved by the measuring circuit in accordance with the invention, the apparatus in accordance with the invention and the methods in accordance with the invention, as defined in the independent claims. Advantageous embodiments are disclosed in the dependent claims.

The invention is based on the idea of enabling the change in the capacitance of at least one part of the measuring circuit with an electric control signal, without any mechanical or other interventions. This opens up the possibility for automatic balancing of the measuring circuit.

Accordingly, the capacitive measuring circuit in accordance with the invention contains one capacitor arrangement to be measured and at least one component with a capacitance that can be changed by at least one control signal.

The term "capacitor arrangement" shall be understood in this specification as being an arrangement with two bodies which can be charged in a non-similar manner by the electrical alternating signal of the alternating signal generator and are separated from one another by at least one dielectric. In a preferred embodiment, the capacitor arrangement concerns a capacitor with two mutually spaced plates, between which air is disposed and between which a moved elongated textile test material can be inserted which is to be examined. The at least one component can be a component of the following group: Variable-capacitance diode, other diode, a plurality of balancing capacitors which are connected in parallel with each other and which can be connected and disconnected with respective electric control signals, especially MEMS capacitors, a reverse-biased transistor, metal-oxide semiconductor field effect transistor, capacitor whose electrode distance can be changed by means of a piezo element. One or several capacitors and/or one or several switches in the at least one component can advantageously be arranged as a micro-electro-mechanical system (MEMS). The measuring circuit can be arranged as a capacitance bridge with at least two bridge arms, with one of the bridge arms being a measuring arm which contains the capacitor arrangement to be measured and at least one other of the bridge arms contains the at least one component.

The measuring circuit in accordance with the invention is preferably used for the capacitive examination of a moved elongated textile test material such as a card sliver, roving, yarn or woven fabric, with the moved test material influencing the capacitance to be measured.

The apparatus in accordance with the invention for the capacitive examination of a moved elongated test material contains a capacitive measuring circuit in accordance with the invention with a measuring capacitor for accommodating the test material and at least one capacitance that can be changed by at least one electric control signal.

The apparatus in accordance with the invention preferably contains means for applying an alternating voltage signal to the measuring circuit for generating an alternating electrical field in the measuring capacitor for the purpose of generating an alternating electrical field in the measuring capacitor, and a through-opening for the test material in the measuring capacitor, which through-opening can be subjected to the alternating electrical field. The measuring circuit can be arranged as a capacitance bridge with at least four bridge arms, with one of the bridge arms containing the measuring capacitor and at least one of the bridge arms comprising the variable capacitance.

In the method in accordance with the invention for operating a measuring circuit, the at least one variable capacitance is changed by at least one electric control signal. During the balancing of the measuring circuit in accordance with the invention, the capacitance to be measured is left substantially unchanged in a temporal respect. The capacitances of the measuring circuit should not change during the balancing, with the exception of the variable capacitance. An electric input signal is applied to the measuring circuit. An electric output signal of the measuring circuit is tapped. The electric control signal is influence by the output signal. The influence on the electric control signal by the output signal preferably occurs automatically in a closed control loop.

The invention is useful for balancing the measuring circuit. The balancing of the measuring circuit can occur in a simple, rapid and cost-effective way thanks to the invention. The device no longer needs to be opened in order to balance the measuring circuit. The balancing can be made at any time. It can automatically be made by the device itself without any intervention by an operator. This allows performing the balancing at any time. A balancing could be performed before each measurement with the measuring circuit, before every $10^{th}$ measurement, or automatically after relevant changes of long-term properties of the output signal or after a larger change of the environmental conditions. This can lead to an increase in the precision, reliability and reproducibility of the measurement, and generally to an improvement in the results of the measurement.

The variable capacitance can be useful not only for the balancing of the measuring circuit. It can also be used for feeding random electric control signals to the measuring circuit. The measuring circuit is detuned in a purposeful manner by means of such control signals. A purposeful detuning of the measuring circuit can have the same or similar effect as a detuning by a change in the capacitance to be measured. Measurements can be simulated by feeding control signals to the measuring circuit via the variable capacitance. The capacitances of the measuring circuit should not change in this process, with the exception of the variable capacitance. Simulated measurements can be used for testing an evaluation circuit and for error searches in the evaluation circuit for example. They can be used for a balancing of the evaluation circuit, e.g. of filters contained in the evaluation circuit. They can also be used for testing and/or setting an apparatus which contains the measuring circuit. It is possible to record the preceding output signals of real measurements with the same measuring circuit or another sensor, store them in a memory and supply them as input signals via the variable capacitance to the measuring circuit. The apparatus can thus be provided with a "record and playback" function.

Accordingly, the capacitance to be measured can be left unchanged in a temporal respect in the method in accordance with the invention and the electric control signal is independent of an output signal of the measuring circuit. The electric control signal is preferably a temporally rapidly changing, synthetically generated and/or previously stored signal. This variant of the method in accordance with the invention is used for example for simulating measurements with the measuring circuit, for testing the measuring circuit or for testing components connected in series with the measuring circuit.

BRIEF DESCRIPTION OF THE DRAWINGS

The invention is explained below in closer detail by reference to the schematic drawings.

DETAILED DESCRIPTION

Figure 1:
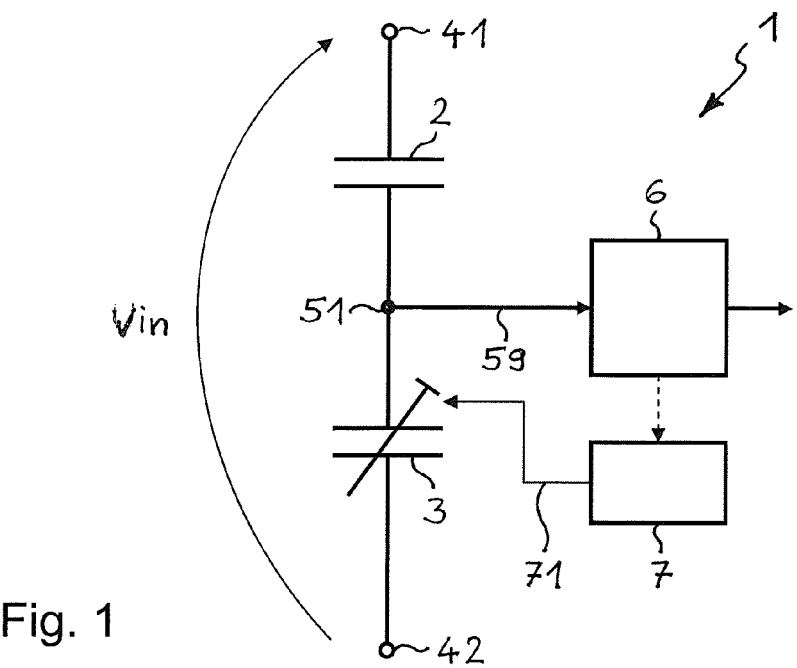
FIGS. 1 to 6 show circuit diagrams of various embodiments of the measuring circuit in accordance with the invention.

The circuit diagram of FIG. 1 shows the basic idea of the invention in a simple manner. A measuring circuit 1 contains a capacitance 2 to be measured and a capacitance 3 which is variable by an electric control signal 71. Possibilities for realizing the electrically variable capacitance 3 will be discussed in connection with FIGS. 3 to 5. The two capacitances 2, 3 are symbolized here schematically by capacitors. They are connected in series one behind the other in this embodiment. Two input connections 41, 42 for applying an electric alternating voltage signal Vin are disposed at the two ends of the series connection, to which measuring circuit 1 is connected. An output connection 51 for the output of an output signal of the measuring circuit 1 is disposed between the two capacitances 2, 3 connected in series. An output line 59 guides the output signal from the output connection 51 to an evaluation unit 6 for the purpose of evaluation.

During the balancing of the measuring circuit 1, notice should be taken that the capacitance 2 to be measured and optionally other capacitances present in the measuring circuit 1 do not change, with the exception of the variable capacitance 3. Ambient conditions such as temperature and air humidity that are constant in time should therefore prevail. If the capacitance 2 to be measured is arranged as a capacitor for accommodating the test material, no test material should be present in the capacitor, or the capacitance of the test material should not change.

An electric alternating voltage signal is applied to the input connections 41, 42 for the balancing of the measuring circuit 1. An electric output signal, preferably an alternating voltage, is tapped from the output connection 51. The variable capacitance 3 is changed by the electric control signal 71, preferably a direct voltage, in such a way that the output signal assumes a specific value, preferably zero. The electric control signal 71 can be set manually by a person, e.g. after the production or during the maintenance of the apparatus in which the measuring circuit 1 is installed. The electric control signal 71 can alternatively be generated automatically. The automatic generation can occur in a control unit 7 specially provided for this purpose or in the evaluation unit 6. FIG. 1 schematically shows a feedback from the evaluation unit 6 to the control unit 7, so that the electric control signal 71 depends on the output signal of the measuring circuit 1. The measuring circuit 1 can be balanced automatically with an automatic generation of the electric control signal 71. There is thus a closed control loop, in which the output signal is the control quantity which is to be controlled to the setpoint value zero, the control unit 7 acts as a controller and the control signal 71 is the actuating value.

Figure 2:
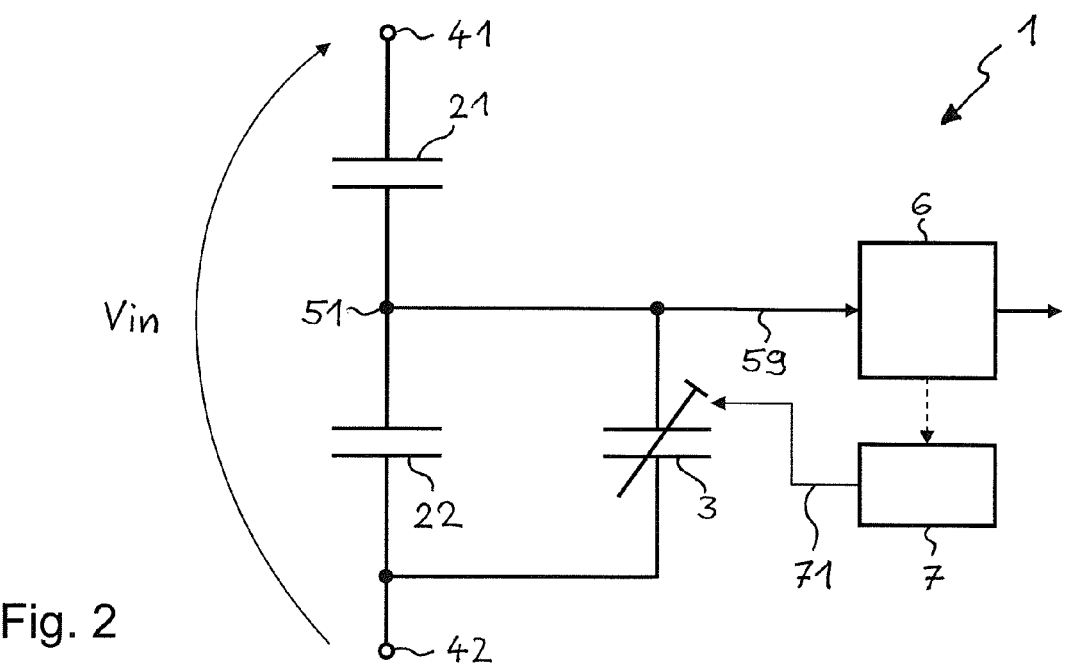

The embodiment of the measuring circuit 1 in accordance with the invention of FIG. 2 differs from the one of FIG. 1 in such a way that it contains a reference capacitor 22 which is connected in parallel to the capacitance 21 to be measured. The reference capacitor 22 is used for more precise measurement and compensation of external influences such as air temperature or air humidity. It is understood that the functions of measuring capacitor 21 and reference capacitor 22 can be switched as required, i.e. the reference capacitor 22 can accommodate test material, whereas the measuring capacitor 21 is without a test material and is used as a reference. The measuring circuit 1 of FIG. 2 is also balanced by applying an electric control signal 71 to the variable capacitance 3.

Figure 3:
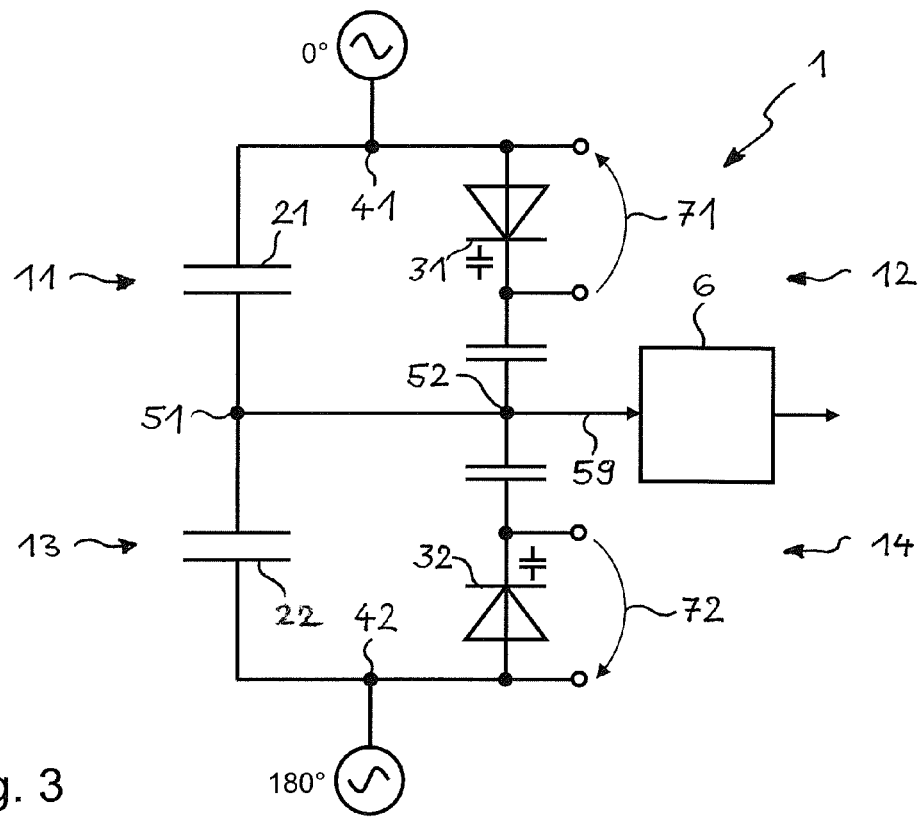

FIG. 3 shows a further embodiment of a measuring circuit 1 in accordance with the invention. It is arranged as a capacitance half measuring bridge. It contains four half bridge arms 11 to 14 which each comprise at least one capacitance. Two half bridge arms 11, 12 and 13, 14 are connected in parallel with each other into pairs of arms, and the two arm pairs 11, 12 and 13, 14 are connected in series with respect to each other. Two input connections 41, 42 are disposed at the two ends of the series connection for applying electric input signals to the capacitance measuring bridge 1. Two mutually connected output connections 51, 52 for the output of an output signal of the capacitance half measuring bridge 1 are disposed between the two series-connected arm pairs 11, 12 and 13, 14. An output line 59 conducts the output signal from the output connections 51, 52 to an evaluation unit 6 for evaluation.

A second bridge arm 12 and a fourth bridge arm 14 have variable capacitances 31, 32. The variable capacitances 31, 32 can each be realized by one variable-capacitance diode (also known as varactor diode or varicap). This is an electronic component whose capacitance can be changed by means of an applied electric voltage. Each of the variable-capacitance diodes 31, 32 is controlled by an analogous electric control voltage 71, 72. In a preferred embodiment, the electric control voltages 71, 72 of the two variable-capacitance diodes 31, 32 are anti-symmetrical direct voltages with respect to a reference voltage, i.e. their differences to the reference voltage are the same according to amount and have opposite signs. The control voltages 71, 72 can be supplied by digital-to-analog converters for example. The capacitance 21 to be measured in the first bridge arm 11 is the capacitance of a measuring capacitor for example which is suitable for accommodating an elongated test material such as a card sliver, roving, yarn or woven fabric (not shown) which is preferably moved in its longitudinal direction. A capacitor 22 which is disposed in the third bridge arm 13 and is connected in series with the measuring capacitor 21 can be provided as a reference capacitor. The reference capacitor 22 allows precise compensation measurements on the test material which are not influenced by external influences such as air temperature or air humidity. The measuring capacitor 21 and the reference capacitor 22 should be as identical as possible in order to have as close as possible to the same capacitances. The two mutually facing capacitor plates of the reference measuring capacitor 21 and the reference capacitor 22 which are at the same electric potential can be realized as a single capacitor plate, thus already removing one source of possible asymmetries.

A first and second alternating voltage signal can be applied for example to the two input connections 41, 42 of the measuring circuit 1 as input signals in the embodiment of FIG. 3. The two applied alternating voltage signals are preferably anti-symmetrical with respect to each other, i.e. their differences to a reference voltage are the same according to amount and phase-shifted by 180° against one another.

An output signal of the measuring circuit 1 is tapped from an output line 59 which forms a half bridge stem, i.e. it connects all four half bridge arms 11 to 14 in the middle of the capacitance half measuring bridge 1. In order to balance the capacitance half measuring bridge 1, the two control voltages are changed in such a way that the output signal assumes the value zero. The two reference voltages are preferably direct voltages and anti-symmetrical with respect to each other concerning a reference voltage. When the capacitance measuring bridge 1 has been balanced, it needs to be ensured that the respective control voltages remain unchanged in measuring operations. The respective values can be stored in a digital memory for example and be supplied as constant voltages via suitable digital-to-analog converters to the variable-capacitance diodes 31, 32. During the balancing of the capacitance half measuring bridge 1 it needs to be ensured that the capacitances of the capacitance half measuring bridge 1 do not change, with the exception of the variable-capacitance diodes 31, 32 which can be changed with the electric control voltages 71, 72.

FIG. 3 shows only one or many possible embodiments of a measuring circuit 1 in accordance with the invention with variable-capacitance diodes 31, 32. The person skilled in the art knows that the circuit environment of the variable-capacitance diodes 31, 32 could also be arranged differently. The variable-capacitance diodes 31, 32 could be replaced by other kinds of variable capacitances. Principally, one single variable capacitance 31 (such as the one in the second half bridge arm 12) would be sufficient in order to balance the capacitance half measuring bridge 1. For reasons of symmetry, the embodiment is more advantageous for most applications with two variable-capacitance diodes 31, 32 according to FIG. 3.

In a further development of this embodiment of the measuring circuit 1 in accordance with the invention, the measuring capacitor 21 in the first half bridge arm 11 and the reference capacitor 22 in the third half bridge arm 13 which can jointly be regarded as a measuring unit can be present several times. The further such measuring units are then switched in parallel to the first measuring unit shown in FIG. 3. They preferably contain capacitors with different capacitances. They can be used for measuring different test materials, e.g. yarns of different thicknesses. The differentiation between measuring and reference capacitor is used in this specification rather for the purpose of unique naming than a rigid assignment of functions, because in most cases a measuring capacitor can also be used as a reference capacitor and vice-versa. If several measuring and reference capacitors are present in a measuring circuit, one of the capacitors is usually used in a measurement as the measuring capacitor and the other capacitors as reference capacitors.

Figure 4:
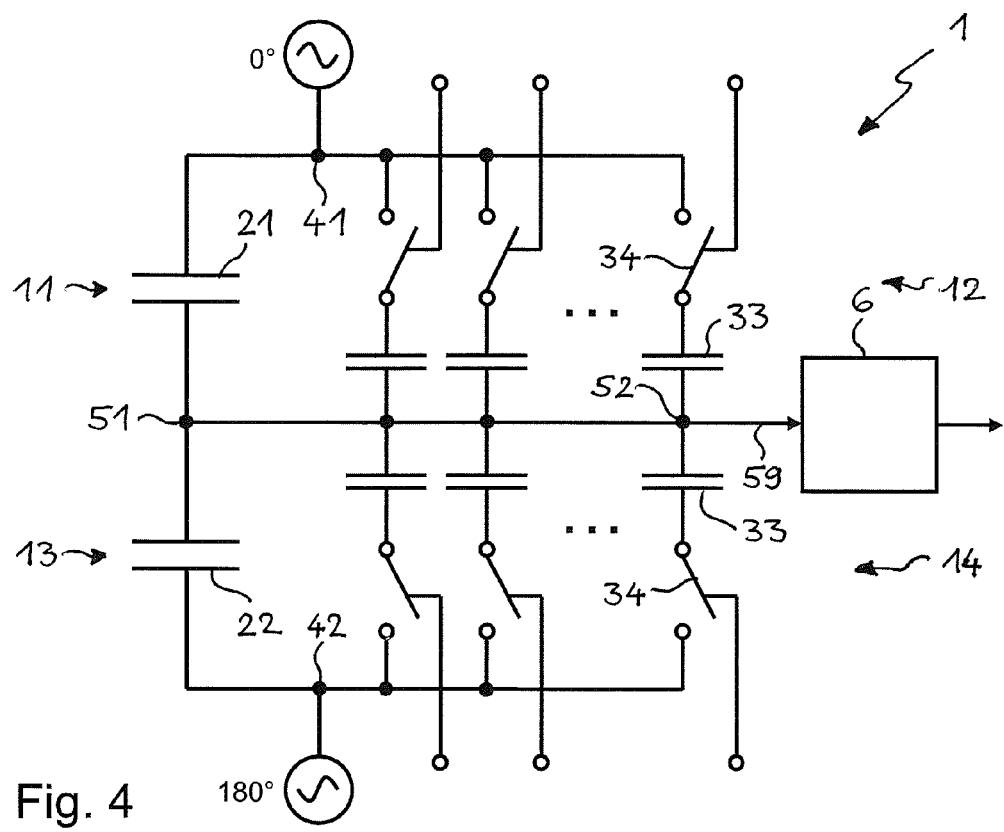

A second embodiment of a measuring circuit 1 in accordance with the invention which is arranged as a capacitance half measuring bridge is shown in FIG. 4. The elements which are analogous to those of the first embodiment of FIG. 3 are provided with the same reference numerals in FIG. 4 and will not be explained anymore. The second embodiment differs from the first one by the realization of the variable-capacitance of the second half bridge arm 12 and the fourth half bridge arm 14. The second half bridge arm 12 and the fourth half bridge arm 14 each contain a plurality of balancing capacitors 33 which are not variable, switched in parallel with respect to each other and can be activated and deactivated with respective electric control signals. As a result, the second half bridge arm 12 and the fourth half bridge arm 14 each have a capacity that can be changed by the control signals. The balancing capacitors 33 can be can be identical or different. In order to cover the largest possible range to be balanced, the balancing capacitors 33 are preferably chosen to be different from one another. For example, every following balancing capacitor 33 could have a capacitance that is half as large as its preceding neighbor. The arrangements of the balancing capacitors 33 in the second half bridge arm 12 and in the fourth half bridge arm 14 are preferably symmetrical with respect to each other.

Every single balancing capacitor 33 can be activated or deactivated by means of a switch 34 associated with the same. The switches 34 are switched by respective digital control signals. The control signals can be supplied by a known digital driver component. In this embodiment too, the switch position required for the balancing needs to be stored and maintained for measuring operations.

There are various known possibilities for realizing the switch 34. When using an additional series capacitor it is also possible to place the balancing capacitors 33 parallel to the switches 34.

The plurality of balancing capacitors 33 in one respective half bridge arm 12, 14 which are connected in parallel with respect to each other can be integrated in one single component. The balancing capacitors 33 are then preferably arranged as a micro-electro-mechanical system, MEMS). An integrated MEMS line arrangement of connectible capacitances is offered for example under the name WSC002L by WiSpry, Inc, Irvine, Calif., USA.

Figure 5:
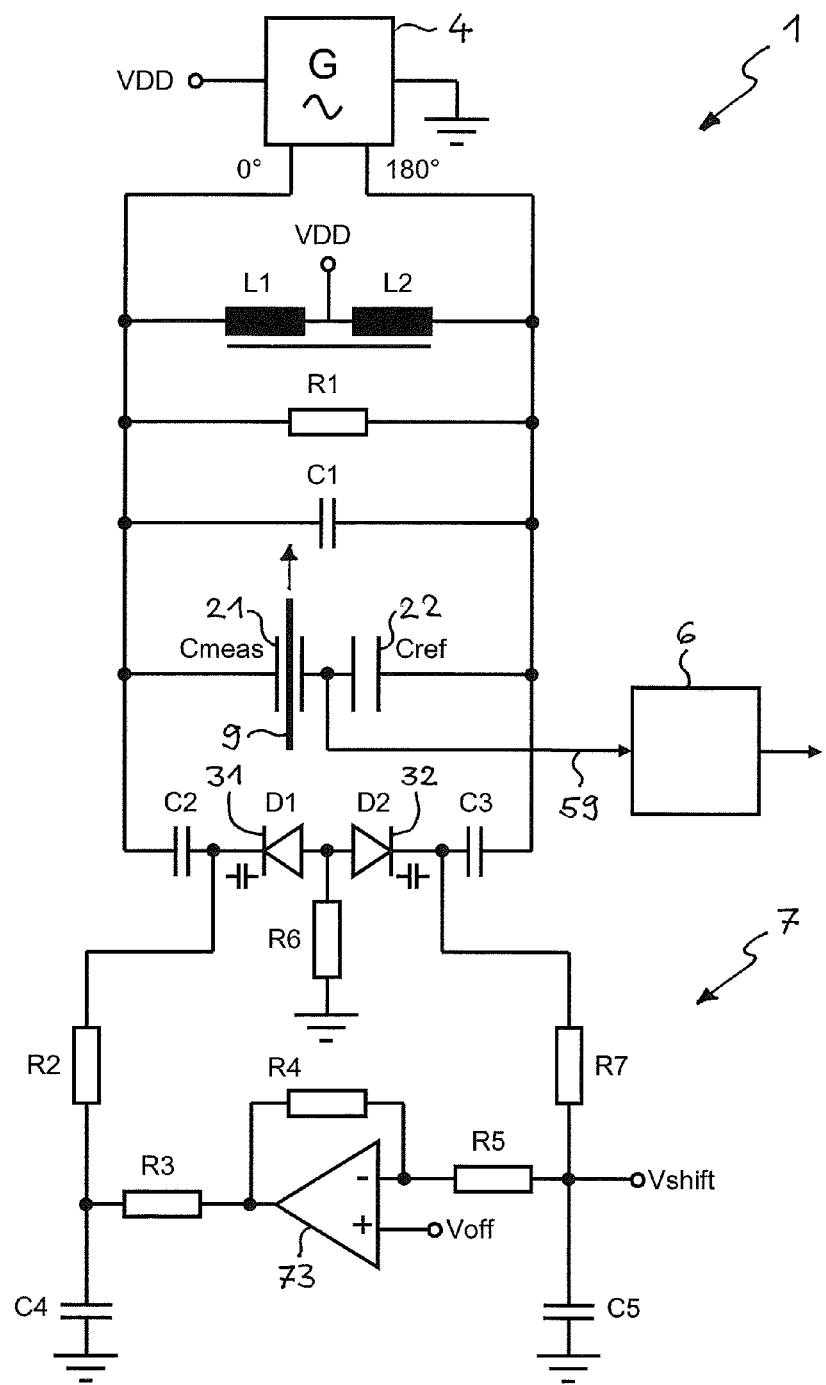

FIG. 5 shows a further embodiment of the measuring circuit 1 in accordance with the invention with variable capacitances 31, 32. The variable capacitances 31, 32 are illustrated here with the circuit symbols for variable-capacitance diodes, but can also be realized in another manner. Such a measuring circuit 1 is preferably used for the capacitive examination of a moved elongated test material 9, e.g. a yarn. The test material 9 passes through a measuring gap which is formed by two preferably planar electrodes of a measuring capacitor 21. A reference capacitor 22 which does not accommodate any measuring subject is connected in series with the measuring capacitor 21. The measuring capacitor 21 and the reference capacitor 22 are parts of an LC resonant circuit 11 which contains two coils L1, L2 which are coupled by a common core, a resistor R1 and a capacitor C1. The resonant circuit 11 is excited by an oscillator 4. The oscillator 4 receives a feed voltage VDD and generates two substantially sinusoidal alternating voltage signals in the two arms of the resonant circuit 11, which signals are phase-shifted by 180° against one another.

For balancing purposes, the measuring circuit 1 comprises two variable capacitances 31, 32 and a control circuit 7 for driving the variable capacitances 31, 32. The core of the control circuit 7 is an amplifier 73, to the one input of which an offset voltage Voff of 2.5 V is applied for example. Furthermore, a shifting voltage Vshift which can be between 0 and 4 V for example is applied to the control circuit 7. The control circuit 7 is arranged in such a way that the control voltages applied to the two variable capacitances 31, 32 are anti-symmetrical direct voltages with respect to each other concerning a reference voltage, i.e. their differences to the reference voltage are the same according to amount and have opposite signs. The reference voltage is substantially set by the offset voltage Voff and the differences by the shifting voltage Vshift. The following preferably applies concerning the resistors used in the control circuit 7: R3<<R2=R6=R7, R4=R5.

Figure 6:
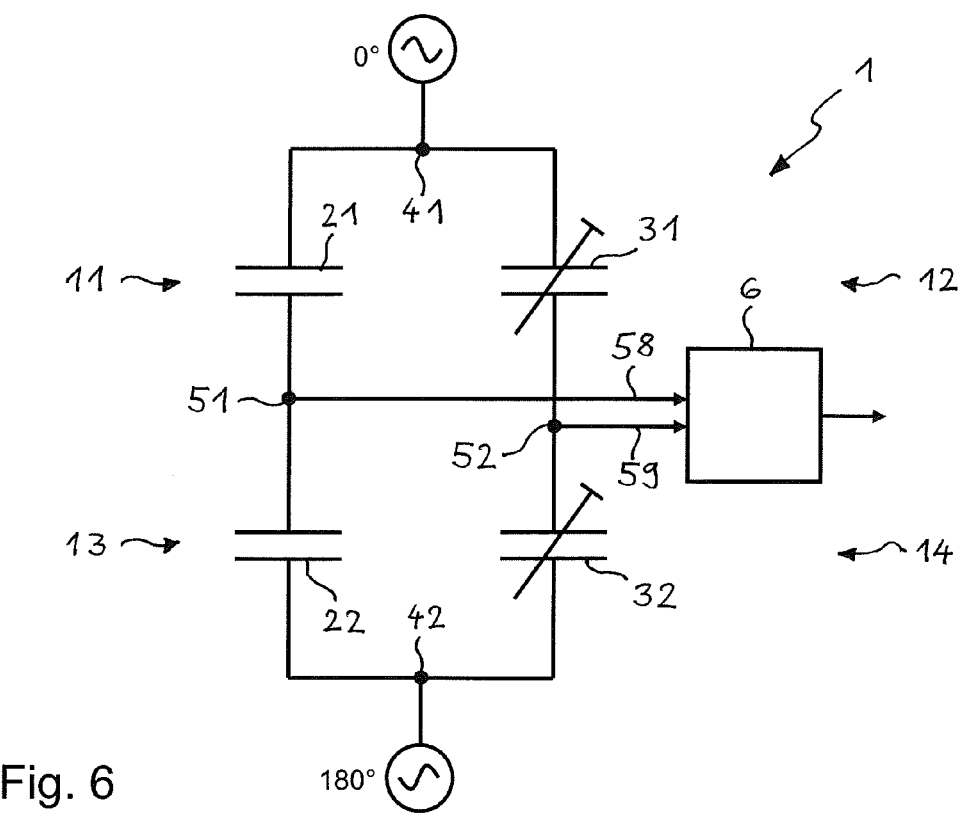

A further development of the measuring circuit of FIG. 3 is the measuring circuit 1 as shown in FIG. 6 and as described below. As already explained above, the same elements which are analogous to the embodiment of FIG. 3 are provided with the same reference numerals in FIG. 6 and will not be explained in further detail here. The main difference to the embodiment of FIG. 3 is that the four bridge arms 11 to 14 are not connected by a bridge stem with each other. As a result, a capacitance full measuring bridge is concerned here, in contrast to the capacitance half measuring bridge of FIG. 3. Two output signals are tapped in the capacitance measuring bridge 1 according to FIG. 6: A first one at the output connection 51 at the connection point between the first bridge arm 11 and the third bridge arm 13, and a second one at the output connection 52 at the connection point between the second bridge arm 12 and the fourth bridge arm 14. The first and second output signals are supplied to the evaluation unit 6 via a first output line 58 and a second output line 59. The evaluation unit 6 determines the difference between the two output signals. It therefore concerns a differential measuring method. The measuring bridge 1 is balanced when the respective difference is zero. One or two variable-capacitances 31, 32 in the second bridge arm 12 and in the fourth bridge arm 14 are used for balancing the measuring bridge 1. They can be arranged as variable-capacitance diodes, as MEMS capacitances or in any other way.

It is understood that the present invention is not limited to the embodiments as discussed above. The person skilled in the art will be able to derive further variants with the knowledge of the invention. Such variants can also be combinations of the embodiments as discussed above for example. The capacitance half bridge in the measuring circuit 1 of FIG. 5 can be replaced by a capacitance full bridge according to FIG. 6. The person skilled in the art knows many electric components whose capacitance can be changed by an electric signal.

LIST OF REFERENCE NUMERALS

1 Measuring circuit
11-14 Bridge arms
2 Capacitance to be measured
21 Measuring capacitor
22 Reference capacitor
3 Variable capacitance
31, 32 Variable-capacitance diodes
33 Balancing capacitors
34 Switch
4 Oscillator
41, 42 Input connections
51, 52 Output connections
58, 59 Output lines
6 Evaluation unit
7 Control circuit
71, 72 Control signals
73 Amplifier
9 Test material

The invention claimed is:
1. An apparatus for the capacitive examination of a moving elongated test material, comprising:
 a capacitive measuring circuit with a measuring capacitor for accommodating the test material, the capacitive measuring circuit arranged as a capacitance measuring bridge with four bridge arms, a first bridge arm designated as a measuring arm that contains the measuring capacitor, a second and a fourth bridge arm that each contain a component with a capacitance that is changeable by at least one electric control signal, and a third bridge arm that contains a reference capacitor.

2. An apparatus according to claim 1, wherein the components comprise at least one of a variable-capacitance diode, other diode, a plurality of balancing capacitors that are connected in parallel with respect to each other and which can be connected and disconnected with respective electric control signals, MEMS capacitors, a reverse-biased transistor, metal-oxide semiconductor field effect transistor, micro-electromechanical capacitor, and a capacitor whose electrode distance is changeable by means of a piezo element.

3. An apparatus according to claim 1, wherein the capacitances of the components are changeable in a substantially anti-symmetrical way with respect to each other.

4. An apparatus according to claim 1, wherein the measuring circuit is arranged as a full capacitance measuring bridge where the four bridge arms are not connected with each other by a bridge stem.

5. An apparatus according to claim 4, further comprising an evaluation unit for determining a difference between a first output signal that is tapped from a connection point between the first bridge arm and the third bridge arm, and a second output signal that is tapped from a connection point between the second bridge arm and the fourth bridge arm.

6. An apparatus according to claim 1, further comprising means for applying an alternating voltage signal to the measuring circuit for generating an alternating electrical field in the measuring capacitor, and a through-opening for the test material in the measuring capacitor, which through-opening is subjectable to the alternating electrical field.

7. A method for the capacitive examination of a moving elongated test material, comprising:

accommodating the test material with a capacitive measuring circuit having a measuring capacitor, the capacitive measuring circuit arranged as a capacitance measuring bridge with four bridge arms, a first bridge arm designated as a measuring arm that contains the measuring capacitor, a second and a fourth bridge arm that each contain a component with a capacitance that is changeable by at least one electric control signal, and a third bridge arm that contains a reference capacitor, and changing the capacitances of the components by applying the at least one control signal to one variable-capacitance diode each.

8. A method according to claim 7, wherein the capacitances of the components are changed by selectively connecting and disconnecting a plurality of balancing capacitors with respective electric control signals, which balancing capacitors are connected in parallel with respect to each other.

9. A method according to claim 7, wherein the capacitances of the components are changed in a substantially anti-symmetrical way with respect to each other.

10. A method according to claim 7, wherein the measuring capacitor is left in a substantially temporally unchanged manner, an electric alternating voltage signal is applied to the measuring circuit, an electric output signal of the measuring circuit is tapped, and the at least one electric control signal is influenced by the output signal.

11. A method according to claim 7, wherein the at least one electric control signal is provided automatically by an output signal in a closed control loop.

12. A method according to claim 7, wherein the measuring capacitor is left in a substantially temporally unchanged way and the at least one electric control signal is independent of an output signal of the measuring circuit.

13. A method according to claim 11, wherein the at least one electric control signal is a temporally rapidly changing signal that is one of synthetically generated and previously stored.

* * * * *